United States Patent [19]

Tiffany

[11] Patent Number: 5,741,877
[45] Date of Patent: Apr. 21, 1998

[54] SILICONE PSEUDOGEL

[76] Inventor: John S. Tiffany, 9490 El Cajon St., Ventura, Calif. 93004

[21] Appl. No.: 870,888

[22] Filed: Jun. 6, 1997

Related U.S. Application Data

[63] Continuation of Ser. No. 570,804, Dec. 12, 1995, abandoned, which is a continuation-in-part of Ser. No. 391,641, Feb. 21, 1995, abandoned.

[51] Int. Cl.$^6$ .................................................. C08G 77/06
[52] U.S. Cl. ........................... 528/15; 528/31; 528/32
[58] Field of Search ............................ 528/15, 31, 32

[56] References Cited

U.S. PATENT DOCUMENTS

| | | | |
|---|---|---|---|
| 4,558,112 | 12/1985 | Talcott | 528/31 |
| 5,079,300 | 1/1992 | Dubrow et al. | 528/15 |
| 5,322,913 | 6/1994 | Blum et al. | 528/15 |

OTHER PUBLICATIONS

Encyclopedia of Polymer Science and Engineering, vol. 3, pp. 296–300 (1985).
Hawley's Condensed Chemical Dictionary, Sax, et al. p. 343 (1987) Van Nostrand Reinhold, N.Y.

*Primary Examiner*—Melvyn I. Marquis
*Attorney, Agent, or Firm*—Michael G. Petit

[57] ABSTRACT

A silicone gel-like material having a reduced content of extractable silicone fluid and having rheological properties approximating human tissue. The gel-like material or "pseudogel" is useful for filling an implantable prosthesis. Prior art silicone gel-filled prosthetic implants contain a high proportion of extractable free silicone fluid. The free silicone fluid within an implant may enter the host's body by diffusion through the prosthetic shell or by rupture of the outer envelope of the prosthesis. The present filler material, or pseudogel, is produced by controlling the cross-linking of the silicone polymer network such that every polymer chain contains only terminal reactive vinyl groups but not all of the reactive groups participate in the cross-linking reaction. In a preferred embodiment, the polymeric vinyl-terminated starting fluids are selected so that the average molecular weights of the polysiloxane polymers comprising the fluid fall into two or three distinct ranges. The cross-linker, which is composed of a siloxane molecule containing silicon hydride groups, is selected to have a relatively low molecular weight and a relatively high Si-H content. By controlling the cross-linker concentration, essentially all the chains can be made to react, but in such a way that chains are only reacted at one end and function as non-extractable diluents between the cross-linked longer chains. The resulting pseudogel exhibits low extractability and is suitable for filling a soft-tissue prosthesis such as a breast prosthesis having a flexible outer shell which contains the pseudogel.

7 Claims, No Drawings

SILICONE PSEUDOGEL

This application is a continuation, of application No. 08/570,804 filed Dec. 12, 1995 now abandoned, which is a continuation-in-part of Ser. No. 08/391,641, filed Feb. 21, 1995, abandoned.

BACKGROUND OF THE INVENTION

1. Field of the Invention

This invention relates to an improved filler material for a prosthetic implant and more particularly to a silicone gel composition.

2. Prior Art

Silicone gels have been used for many years for filling soft medical implants such as breast prostheses. A gel normally consists of a polymeric network which is cross-linked to substantially contain a viscoelastic portion and a fluidic or extractable portion. In a prosthesis, the gel is usually contained within a flexible elastomic shell which imparts structural integrity to the prosthesis. A recurring problem with such silicone gel-filled prostheses is "gel-bleed" or extraction of the fluidic portion of the gel from within the prosthesis with subsequent penetration of the surrounding tissue by the fluidic portion. The choice of fluidic portion determines the stiffness or firmness of the gel.

To overcome the problem of "gel-bleed", shells for enveloping and containing the gel have been developed comprising a barrier coating or membrane having a high percentage of phenyl silicone or diphenlysilicone which substantially impedes the flow of the fluidic component of the prior art silicone gel through the barrier layer and, thus, through the shell. Such a barrier membrane is disclosed for example in U.S. Pat. No. 4,455,691 to Compton and Redinger.

Recently, soft implant manufacturers and physicians have turned away from silicone gel-filled implants in favor of saline filled implants because of alleged autoimmune diseases effecting some prosthesis recipients and claimed to be a result of "gel-bleed." Notwithstanding the foregoing, it is generally accepted that a soft tissue prosthesis comprising a silicone gel-filled implant is aesthetically more pleasing than a saline filled prosthesis and possesses fluidic properties that more closely approximate the fluidic properties of human tissue rendering silicone gel a particularly desirable fill material. Consequently, it would be of great value to provide a gel-like filler material having rhelogical properties similar to the silicone gel currently used as fillers and which does not have a fluidic component which is significantly extracted from the prosthesis following implantation of the prosthesis within the body of a patient.

Talcott, in U.S. Pat. No. 4,558,112, hereinafter "'112", discloses a low-oiling siloxane gel composition suitable for use as a filler for a gel-filled implant. The gel is characterized as being the addition product of a monofunctional first prepolymer and a second prepolymer which possesses "several" vinyl groups in the chain in addition to the terminal vinyl group. Talcott, in '112, relies on the use of n-butyllithium as a reagent for producing the monofunctional (vinyl) silicones required for the gel formulation. The highly basic nature of butyllithium can cause side reactions rendering functionality greater than one for these type of compounds. The gels disclosed by Talcott in accordance with '112 preferably contain 60% free unreacted fluid. Talcott teaches extracting the intermediate polymeric silicones in order to remove free low molecular weight silicones therefrom. This extraction step renders the '112 teaching impractical for commercially producing a low-extractable gel suitable for filling an implantable prosthesis.

SUMMARY OF THE INVENTION

It is a primary object of the invention to provide a gel-like material, or "pseudogel" suitable for filling a soft-tissue prosthesis which pseudogel comprises less than about 15% extractable fluids. The present method for making a pseudogel employs only difunctional prepolymers to prepare a gel-like cross-linked silicone structure having a low extractable component and which does not require extraction of free low molecular weight silicones from the intermediate molecular weight silicones prior to cross-linking.

It is another object of the invention to provide a silicone gel comprising less than about 15% extractables. The term "extractables", as used hereinthroughout with reference to a gel or gel-like substance such as pseudogel, refers to the unreacted portion of the gel which is generally fluidic and free to migrate out of the gel at body temperature of 38° C. and, more specifically, refers to the unreacted fluid portion of a gel which is extracted by organic solvents such as xylene, hexane or trichloroethane at temperatures around 20° C.–40° C.

It is yet another object of the invention to provide a gel comprising a viscoelastic portion which has a high polydispersity by cross-linking polymers having a polymodal weight distribution and, more particularly, either a bimodal or a trimodal molecular weight distribution.

Gels are usually defined as polymer networks, either covalently or ionically cross-linked, which are swollen by fluid to some predetermined volume. A pseudogel in accordance with the present invention is a gel-like material produced by controlling the cross-linking of a polymer network such that every polymer chain contains terminal reactive vinyl groups but not all the reactive groups are allowed to participate in the cross-linking reaction. The polymeric vinyl-terminated starting fluids are selected so that the molecular weight distribution of the polymeric fluid components is polydisperse such that the average molecular weights of the reactive polymers fall into more than one distinct range. In addition, the cross-linker, which is composed of a siloxane molecule containing silicon hydride groups is controlled to have a relatively low molecular weight and a relatively high Si-H content. This combination of starting materials results in a network in which there is a low cross-link density and in which the cross-links are concentrated in foci with long chains therebetween.

Essentially all the chains can be made to react, but by controlling the cross-linker concentration, many of the chains, particularly the short and medium length chains, will only react at one end so that they function as a trapped diluent between the cross-linked longer chains. Since these chains are less restricted, they impart to the final cured mass a consistency similar to a classical gel but without the extractable component. Curing of the mass is accomplished in the usually manner with the addition of 0.1 to 10 ppm by weight of a platinum compound. It is important that the reactive siloxane chains have only terminal vinyl groups and no reactive vinyl siloxane groups along the intervening chain.

The features of the invention believed to be novel are set forth with particularity in the impending claims. However, the invention itself, both as to organization and method of operation, together with further objects and advantages thereof may best be understood by the following description of the preferred embodiments.

DESCRIPTION OF THE PREFERRED EMBODIMENTS

The present invention describes a new type of silicone gel (pseudogel) having a substantially reduced amount of extractable silicone. It is an advance over current state-of-the-art gels. While the method for making pseudogel uses the same general reaction chemistry as currently employed to make prior art silicone gels, the selection of the component silicone polymer reactants disclosed below provides an improved gel product. A brief discussion of conventional gel technology is required in order to appreciate the advance in the art of the present invention. Conventional silicone gel is chemically produced by combining three silicone polymer components and causing a gellation reaction to occur. These components include two reactive silicones: (a) a silicone polymer modified to contain carbon-carbon double bonds (vinyl groups), which have been distributed internally among the dimethylsiloxy chain-extending units along the polymer chain; and (b) a silicone polymer cross-linker, modified to contain silicon-hydrogen bonds (Si-H groups). Each of the above polymers is a collection of long-chain molecules of varying length. During the gellation process the above two polymers react with one another to form the cross-linked "network" or "matrix" comprising the final gel.

A third non-reactive silicone polymer (polydimethylsiloxane) is added to the mixture prior the gellation reaction in order to provide the "mobile" phase of the final gel. When the gellation reaction occurs, this third component does not form physical chemical bonds thereby affixing it to the silicone gel "network". Rather, since it is a long-chain polymer, it becomes entangled in the cross-link network. This phenomenon of entanglement holds the free silicone polymer in the gel and is a key element of providing the gel-like properties of the final product.

In a slightly modified version of the above technology the third, non-reactive silicone is not added explicitly to the formulation. Silicone polymers are commercially manufactured by a process in which the chain-extending, internal units of the polymer are randomly and statistically placed. Since the polymer chain-extending units of the first reactive polymer, above, include both dimethylsiloxy units and a smaller number of vinyl group modified units, statistics dictate that some of the polymer molecules manufactured will contain no vinyl group modification. These molecules (containing no vinyl groups) are non-reactive polydimethylsiloxane identical to the third component above and are present as a by-product of the silicone polymer manufacturing process. By choosing the manufacturing parameters appropriately an amount of this non-reactive material can be intentionally generated in sufficient quantity to preclude the need to explicitly add additional polydimethylsiloxane. Gel properties of the final product are achieved with this historical approach.

The term "pseudogel," as used hereinthroughout, refers to a cross-linked polyorganosiloxane having viscoelastic properties similar to silicone gels but substantially lacking an extractable fluid or "swelling component." The term "gel-like" as used hereinthroughout refers to cross-linked silicone polymers and having tactile properties resembling human soft tissue, particularly breast tissue.

Silicone pseudogel is produced chemically by combining two silicone polymer components and causing a gellation reaction to occur. Both of these components are reactive silicones: (a) a silicone polymer modified to contain carbon-carbon double bonds (vinyl groups), which vinyl groups are attached at the termini (ends) of a dimethylsiloxy polymer chain; and (b) a silicone polymer cross-linker, modified to contain silicon-hydrogen bonds (Si-H groups). During the gellation process the above two polymers react with one another to form the cross-linked "network" or "matrix" of the final gel. No non-reactive silicone polymer (polydimethylsiloxane) is added to the mixture. A conventional, free mobile phase is not a part of the formulation.

The production of pseudogel in accordance with the present invention is conveniently presented by means of examples which set forth with particularity the preferred ranges of concentrations of reactants and conditions for optimizing the properties of the resultant gel or "pseudogel" for medical implant applications. Silicone pseudogel is made by preparing a mixture of a polymer such as polysiloxane, each polysiloxane polymer chain comprising $(CH_3)_2SiO$ groups and terminating with $(CH_3)_2ViSiO_{0.5}$ end groups; Vi indicating a vinyl group.

As a first example, the polymer mixture is a polyorganosiloxane fluid having a viscosity of 1,500–10,000 centipose and which fluid includes silicone polymers having a trimodal molecular weight distribution comprising 25 parts of polymer having a viscosity of 500 centipoise (and having reactive terminal vinyl groups), 25 parts of polymer having a viscosity of 140,000 centipoise (also having terminal vinyl reactive groups), and 50 parts of polymer having a viscosity of 2000 centipoise (which also has terminal reactive vinyl groups). All viscosities presented herein are measured at 20° C. This fluidic mixture of polymers is cross-linked by the addition of a siloxane cross-linker having a viscosity between 25 and 100 centipoise (at 20° C.) and a methlyhydrogen-siloxane content of between 25 and 100 mole percent. The siloxane cross-linker is preferably a hydrogen siloxane fluid. That is, the cross-linker comprises hydrogen siloxane consisting of $(CH_3)_2SiO$ and $(CH_3)HSiO$ groups such that the $(CH_3)HSiO$ groups are from 25–100 mole percent and the terminal groups being either $(CH_3)_3SiO_{0.5}$ or $(CH_3)_2HSiO_{0.5}$. The catalyst used to form the pseudogel is preferably a complex of chloroplatinic acid and cyclic vinylsiloxanes containing less than 5 ppm of platinum metal in the total mix by weight. The platinum catalyst is an organic complex of hexachloroplatinic acid. The possible complexing agents include alcohols, ethers, aromatic compounds and vinyl-containing siloxanes. The preferred complexing agents in this case are tetravinyltetramethylcyclotetrasiloxane or divinyltetramethyldisoloxane. The temperature range for carrying out the cross-linking reaction is 20° C.–160° C. and preferably around 120° C.

As a second example, a pseudogel composition can be made by reacting a mixture comprising: (a) a polyorganosiloxane fluid having a viscosity of from 1,500 to 10,000 centipoise and wherein the polyorganosiloxane fluid comprises polyorganosiloxane molecules having molecular weights which fall substantially into three ranges with about 15%–40% of the fluid by weight has an average molecular weight of from 1,000 to 3,000 daltons, 15%–40% of the fluid by weight has an average molecular weight of form 100,000 to 200,000 daltons and from 40%–60% of the polyorganosiloxane molecules have an average molecular weight of from 3,000 to 20,000 daltons and wherein the polyorganosiloxane polymer chains are composed entirely of $(CH_3)_2SiO$ groups with $(CH_3)_2ViSiO0.5$ end groups, (b) a hydrogen siloxane fluid having a viscosity of 25° C. of from 25 to 100 centipoise and comprised of $(CH_3)_2SiO$ and $(CH_3)HSiO$ groups such that the $(CH_3)HSiO$ groups are from 25 to 40 mole percent and wherein the terminal groups are either $(CH_3)_3SiO_{0.5}$ or $(CH_3)_2HSiO_{0.5}$, and (c) a platinum complex catalyst in an amount sufficient to furnish not more than 10 ppm of platinum based on the combined weights of (a) and (b), the proportions of (a) and (b) being such that the ratio of silicon hydride groups in (b) to vinyl groups in (a) is from 0.6 to 0.85, the reaction product being a pseudogel.

Although the above examples and the preceding specification has described cross-linking a polymer fluid comprising a mixture of polymers which fall within substantially three distinct molecular mass groups (i.e. the fluid has a trimodal molecular weight distribution), it has been found that a broader range of molecular masses may be used without detracting substantially from the properties of the product. That is to say, the range of molecular weights may vary considerable but should preferably be within a particular range. A single fluid having an average molecular weight of from 25,000 to 100,000 daltons and a polydispersity of at least 5 and preferably 8 will produce a pseudogel having similar properties of fluidity and low extractability.

For example, a fluid containing vinyl-terminated polysiloxane chains having a viscosity of 14,000 centipoise (20° C.) and an average molecular mass of 70,000 daltons contains 82% of polymer with molecular mass between 6,000 and 730,000 daltons of which 5% falls between 52,000 and 120,000. The polydispersity is defined as the ratio of the weight average molecular weight to the number average molecular weight. The polydispersity of this fluid is approximately 8. It is important that a material comprised of multiple separate fluids or comprised of 1 fluid with a high polydispersity is used to assure that there will be chains of both high and low molecular weights contained therein. The hydrogen siloxane cross-linker used to cross-link the triphasic fluid referenced above may also be employed to cross-link the polydisperse fluid.

As a third example, a pseudogel having a particularly low percentage of extractable fluidic component (less than 15%) is made as above but using a silicone polymer mixture comprising 80 parts by weight of 100 cSt fluid and 20 parts by weight of 30,000 cSt fluid (viscosities at 20° C.). The important feature here is the use of two fluid polyorganosiloxane polymers which have highly disperse, widely separated, average molecular weights, and are bifunctional, each silicone polymer chain in the fluid mixture having reactive vinyl groups only at the terminal ends of the chain.

Two key advancements in the art are responsible for the success of creating pseudogel technology. First, the use of vinyl group modification at the termini of the silicone polymer (as opposed to the internal chain-extending placement of the vinyl units) assures that each and every molecule of this polymer contains two vinyl units and is reactive. Thus molecules containing no vinyl group units are not intentionally manufactured in the process, and the conventional free, mobile low molecular weight silicone discussed earlier, is not created.

The second advancement in the art is the creation of a novel material having gel-like properties without the addition of a free, mobile phase. The polymers used to manufacture silicone pseudogel are long and "floppy". Constraining or anchoring one end of such a polymer will still allow the other end to move about. When the two components are reacted some of the vinyl group-containing polymers will react at both ends (forming the network) and some will react only at one end. It is the mobility of the free ends of the molecule which provides the gel-like properties to the final product.

A variety of gels can be produced with varying firmness. The firmness of the gel is controlled through design of the specific polymers. The molecular weight of the polymers, as well as the extent of Si-H group modification determines these properties. Sufficient cross-linking (ratio of the two components and composition of the Si-H group containing component) is required to assure that the vinyl group modified polymers have reacted at least once. Molecular weight control of the polymers assures aesthetics of the gel. The pseudogel is relatively firm with extractable silicone levels of about 10% (as opposed to 50%–60% in conventional gels).

While particular embodiments of the present invention have been illustrated and described, it would be obvious to those skilled in the art that various other changes and modifications can be made without departing from the spirit and scope of the invention. The important feature of the invention is employing polysiloxane polymers falling within a particular size range and having only terminal vinyl groups which, when cross-linked with a siloxane molecule as specified below, have gel-like properties with a reduced "fluidic" or unreactive extractable portion. It is therefore intended to cover in the impending claims all such changes and modifications that are within the scope of this invention.

What I claim is:

1. A pseudogel consisting of a viscoelastic material having a gel-like consistency, said material comprising a network of polydisperse terminally cross-linked polyorganosiloxane polymer chains and containing less than about a 15 percent fluid portion which is capable of being extracted by organic solvents at 20° C. to 40° C., said viscoelastic material having a polydispersity of at least 5.

2. A filler material for a medical implant comprising a pseudogel in accordance with claim 1.

3. A composition of matter consisting of a pseudogel made by reacting a mixture comprising: (a) a polyorganosiloxane fluid having a viscosity of from 1,500 to 10,000 centipoise and wherein the polyorganolsiloxane fluid comprises polyorganosiloxane polymer chains having molecular weights which fall substantially into three ranges, wherein about 15%–40% of the polyorganosiloxane polymer chains by weight have an average molecular weight of from 1,000 to 3,000 Daltons, about 15%–40% of the polyorganosiloxane polymer chains by weight have an average molecular weight of from 100,000 to 200,000 Daltons, and about 40%–60% of the polyorganosiloxane polymer chains have an average molecular weight of from 3,000 to 20,000 Daltons and wherein the polyorganosiloxane polymer chains are composed entirely of $(CH_3)_2SiO$ groups with $(CH_3)_2ViSiO_{0.5}$ end groups, wherein Vi indicates a vinyl group and the chains include no internally placed vinyl groups, (b) a hydrogen siloxane fluid having a viscosity at 25° C. of from 25 to 100 centipoise and comprised of $(CH_3)_2SiO$ and $(CH_3)HSiO$ groups such that the $(CH_3)HSiO$ groups are from 25 to 40 mole percent and wherein the terminal groups are either $(CH_3)_3SiO_{0.5}$ or $(CH_3)_2 \cdot HSiO_{0.5}$, and (c) a platinum complex catalyst in an amount sufficient to furnish not more than 10 ppm of platinum based on the combined weights of (a) and (b), the proportions of (a) and (b) being such that the ratio of silicon hydride groups in (b) to vinyl groups in (a) is from 0.6 to 0.85, the reaction product being a pseudogel.

4. The composition of matter of claim 3 wherein said mixture is reacted at a temperature between 20° C. and 160° C.

5. A composition of matter consisting of a pseudogel made by reacting a mixture comprising: (a) a polyorganosiloxane fluid comprising polyorganosiloxane polymer chains having molecular weights which fall substantially into two ranges with 80% of the fluid by weight having a viscosity of 100 cSt at 20° C. and 20% of the fluid by weight has a viscosity of about 30,000 cSt at 20° C. and wherein the polyorganosiloxane polymer chains are composed entirely of $(CH_3)_2SiO$ groups with $(CH_3)_2ViSiO_{0.5}$ end groups, wherein Vi indicates a vinyl group and the chains include no internally placed vinyl groups, (b) a hydrogen siloxane fluid having a viscosity at 25° C. of from 25 to 100 centipoise and comprised of $(CH_3)_2SiO$ and $(CH_3)HSiO$ groups such that the $(CH_3)HSiO$ groups are from 25 to 40 mole percent and wherein the terminal groups are either $(CH_3)_3SiO_{0.5}$ or $(CH_3)_2HSiO_{0.5}$, and (c) a platinum complex catalyst in an amount sufficient to furnish not more than 10 ppm of platinum based on the combined weights of (a) and (b), the proportions of (a) and (b) being such that the ratio of silicon hydride groups in (b) to vinyl groups in (a) is from 0.6 to 0.85, the reaction product being a pseudogel.

6. The composition of claim 5 wherein said mixture is reacted at a temperature between 20° C. and 160° C. to yield a pseudogel reaction product.

7. The pseudogel of claim 1, wherein said viscoelastic material has a polydispersity of approximately 8.

* * * * *